US008815236B2

(12) United States Patent
Burke et al.

(10) Patent No.: US 8,815,236 B2
(45) Date of Patent: Aug. 26, 2014

(54) METHOD FOR TREATING MULTIPLE SCLEROSIS AND CROHN'S DISEASE

(71) Applicant: Biogen Idec MA, Inc., Cambridge, MA (US)

(72) Inventors: David J. Burke, Oakland, CA (US); Shaun E. Buckley, San Francisco, CA (US); Sherwood Russ Lehrman, Los Altos, CA (US); Barbara Horsey O'Connor, San Carlos, CA (US); James Callaway, San Diego, CA (US); Christopher P. Phillips, Doyleston, PA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 13/676,866

(22) Filed: Nov. 14, 2012

(65) Prior Publication Data

US 2013/0071386 A1    Mar. 21, 2013

Related U.S. Application Data

(60) Division of application No. 12/572,978, filed on Oct. 2, 2009, now Pat. No. 8,349,321, which is a continuation of application No. 10/773,406, filed on Feb. 9, 2004, now abandoned.

(60) Provisional application No. 60/445,818, filed on Feb. 10, 2003.

(51) Int. Cl.
*A61K 39/395* (2006.01)

(52) U.S. Cl.
USPC .................................... 424/130.1; 424/133.1

(58) Field of Classification Search
None
See application file for complete search history.

(56) References Cited

U.S. PATENT DOCUMENTS

| 4,597,966 | A | 7/1986 | Zolton et al. |
| 5,840,299 | A | 11/1998 | Bendig et al. |
| 5,945,098 | A | 8/1999 | Sarno et al. |
| 6,448,225 | B2 | 9/2002 | O'Connor et al. |
| 6,914,128 | B1 | 7/2005 | Salfeld et al. |
| 2002/0192282 | A1 | 12/2002 | Beckert et al. |
| 2003/0113316 | A1 | 6/2003 | Kaisheva et al. |
| 2004/0170632 | A1 | 9/2004 | Mahler et al. |
| 2008/0286280 | A1 | 11/2008 | Kallmeyer et al. |
| 2008/0311119 | A1 | 12/2008 | Maloney |
| 2012/0134989 | A1 | 5/2012 | Maloney |
| 2013/0017193 | A1 | 1/2013 | Maloney |

FOREIGN PATENT DOCUMENTS

| EP | 1 475 100 | 11/2004 |
| JP | 2001-503781 | 3/2001 |
| JP | 2003-526655 | 3/2001 |
| WO | WO 98/56418 A1 | 12/1988 |
| WO | WO 97/04801 A1 | 2/1997 |
| WO | WO 97/45140 | 12/1997 |
| WO | WO 98/22136 | 5/1998 |
| WO | WO 00/56722 | 9/2000 |
| WO | WO 02/12501 | 2/2002 |
| WO | WO 03/007988 | 6/2002 |
| WO | WO 03/009817 | 2/2003 |
| WO | WO 03/068259 | 8/2003 |

OTHER PUBLICATIONS

Natalizumab Product Information, 2010, p. 1-16.*
Fiona H. Gordon et al., "A Randomized Placebo-Controlled Trial of a Humanized Monoclonal Antibody to α4 Integrin in Active Crohn's Disease", Gastroenterology 2001, vol. 121, No. 2, pp. 268-273.
Search Report dated May 12, 2009 (One (1) page).
Cleland, Jeffrey L. et al., "The Development of Stable Protein Formulations: A Close Look at Protein Aggregation, Deamidation, and Oxidation", Critical Review in Therapeutic Drug Carrier Systems, 10 (4):307-377 (1993).
Levine H L, et al.: "The use of surface tension measurements in the design of antibody-based product forumulations" Journal of Parenteral Science and Technology 1991 United States, vol. 45, No. 3, 1991, pp. 160-165.
Kuby, Immunology, 1991, p. 514.
Gordon et al., Gastroenterology, 2001, 121:268-74.
Engelhardt et al., Eur. J. Immunology, 2005, 35:2268-2273.
W. A. Sheremata, et al., "A safety and pharmacokinetic study of intravenous natalizumab in patients with MS", Official Journal of the American Academy of Neurology, Mar. 23, 1999, pp. 1072-1074, vol. 52, No. 5.
Wei Wang, "Instability, stabilization, and formulation of liquid protein pharmaceuticals", International Journal of Pharmaceutics, Aug. 20, 1999, pp. 129-188, vol. 185, No. 2, ISSN 0378-5173.
Japanese Office Action of JP 2006-503453 dated Aug. 13, 2010.
Canadian Office Action of CA 2,515,444 dated Mar. 4, 2011.
Response to exam report dated Jan. 30, 2013 in EP 08771026.5.
Response to exam report dated Apr. 27, 2012 in NZ 582436.
Response to exam report dated Oct. 3, 2011 in NZ 582436.
Response to office action dated Jun. 29, 2011 in U.S. Appl. No. 12/139,362.
Response to office action dated Jun. 23, 2010 in U.S. Appl. No. 12/139,362.
Response to office action dated Mar. 1, 2011 in U.S. Appl. No. 12/139,362.

* cited by examiner

*Primary Examiner* — Yunsoo Kim
(74) *Attorney, Agent, or Firm* — Yuko Soneoka; Arnold & Porter LLP

(57) ABSTRACT

A stable aqueous pharmaceutical formulation comprising a therapeutically effective amount of an antibody, polysorbate 80, a buffer which inhibits polysorbate oxidation is described along with methods of making the preparation. Also described are formulations with high antibody concentrations which maintain fixed volumes and which may be used on patients of variable weight.

22 Claims, No Drawings

US 8,815,236 B2

METHOD FOR TREATING MULTIPLE SCLEROSIS AND CROHN'S DISEASE

CROSS-REFERENCE TO RELATED APPLICATIONS

This application is a divisional of U.S. application Ser. No. 12/572,978, filed Oct. 2, 2009, now U.S. Pat. No. 8,349,321, which is a continuation of U.S. application Ser. No. 10/773, 406, filed Feb. 9, 2004, which claims priority under 35 U.S.C. §119 to U.S. Provisional Application No. 60/445,818 entitled "Immunoglobulin Formulation and Method of Preparation Thereof" and filed on Feb. 10, 2003, the entire contents of which are hereby incorporated by reference in their entirety.

FIELD OF THE INVENTION

The invention is directed to stable, concentrated formulations of proteins or antibodies, such as natalizumab, wherein the activity of the antibody is retained and also can be administered in a small volume and can be administered to a subject of variable weight in need thereof.

BACKGROUND OF THE INVENTION

Antibody and protein formulations are known in the art. However, preparing protein formulations, such as antibody formulations, which are chemically and biologically stable, are fraught with challenges. Preparing formulations which are also not only stable but can maintain a small volume (i.e., allowing for a small volume injection) even with an increased concentration of protein, such as antibody, also is problematic. The need for such formulations exist. For example, concentrated amounts of protein in a fixed volume that is also stable would be especially beneficial to patients of variable weight. Administration of fluids to patients of variable weights may, for example, have an adverse reaction. Development of such formulations has been hindered by the proteins or the antibodies themselves, which have a high tendency to aggregate and precipitate.

SUMMARY OF THE INVENTION

Therefore, notwithstanding what has previously been reported in the literature, there exists a need for improved methods of formulating proteins and/or antibodies. There is also a need for stable formulations with large concentrations of antibody or protein, where the activity of the antibody or protein is retained. Also needed are stable formulations of concentrated protein which maintain a fixed volume. Applicants disclose herein stable compositions which can be further utilized to prepare antibody formulations, especially formulations with high concentrations of antibody which do not precipitate out and are stable when stored at the recommended temperatures. The highly concentrated and stable antibody formulations will greatly aid physicians in treating subjects of variable weights.

One aspect of the invention provides for a stable, aqueous pharmaceutical formulation comprising an immunoglobulin (or other protein), a phosphate buffer, a polysorbate, and sodium chloride. Preferably the polysorbate is polysorbate 80, and preferably in the amount of about 0.001% to about 2.0% (w/v). Most preferably the polysorbate is present in the amount of about 0.02%. In another embodiment, the immunoglobulin or other protein is present in the formulation in an amount of about 0.1 mg/mL to about 200 mg/mL. Preferably the formulation is buffered to a pH between about 3.0 and about 7.0 and most preferably is about 6.0∀0.5. The formulation is preferably isotonic. The formulation may further comprise histidine. Preferably, the histidine is L-histidine.

In another aspect of the invention, the immunoglobulin of the above formulation is an anti-alpha-4 integrin antibody, such as natalizumab or another humanized antibody or monoclonal antibody. This antibody can be present in a standard amount or in a concentrated amount, e.g., about 15 mg/mL or more. Preferably, the natalizumab is present in an amount from about 20 mg/mL to about 150 mg/mL. In instances wherein the formulation is present in a concentration of about 15 mg/mL or more, this formulation is maintained in a fixed volume, for example, of about 125 mL.

It is a further object of the invention to provide a method of treating a patient with variable weight for a condition with a therapeutic amount of an immunoglobulin comprising administering a formulation as described above and herein, wherein the condition is treated by administration of the formulation. It is a further aspect of the invention that the condition be one that is mediated by alpha-4 integrin, and in such conditions the immunoglobulin is one which recognizes and binds to alpha-4 integrin, such as natalizumab.

A further aspect of the invention provides for a composition comprising a sodium phosphate, a polysorbate, a protein and NaCl with a pH of 6.0∀0.5, wherein the composition is stable when stored at 5EC to 8EC for a long period of time.

Another aspect of the invention provides for a method of preparing a stable protein containing formulation comprising admixing sodium phosphate, sodium chloride, a polysorbate and a protein and adjusting the pH of the mixture with phosphoric acid to about pH 6.0∀0.5.

The protein may be lyophilized in the formulation of the present invention. The polysorbate is preferably polysorbate 80 k, present in an amount of about 0.02% (w/v), and the protein is preferably natalizumab. The formulation may further comprise histidine.

Preferably, the protein is lyophilized in a solution comprising 5 mM histidine, 20 mg/mL sucrose and 0.02% polysorbate 80 at a pH 6, and the protein is natalizumab at a concentration of 20 mg/mL.

It is a further object of the invention to provide for an article of manufacture comprising a container holding the stable formulation described above and herein.

Another aspect of the invention provides for a method for treating a patient with variable weight for a condition, comprising simultaneously or sequentially administering to the patient a therapeutically effective combination of a formulation described above and herein and a compound or therapy effective against the condition.

It is a further aspect of the invention to provide a use of any of the stable formulations described herein for the preparation of a medicament for the treatment of a condition wherein the medicament is effective to treat said condition. This medicament may further comprise a second compound or therapy to treat the condition.

DETAILED DESCRIPTION OF THE PREFERRED EMBODIMENTS OF THE INVENTION

1. Definitions

By "protein" is meant to include but is not limited to immunoglobulins, enzymes, receptor, and fragments thereof. Although discussion of the formulation is provided mainly in reference to an antibody or immunoglobulin, other proteins are contemplated as interchangeable in the formulations disclosed.

By "immunoglobulin" is meant to include but is not limited to an antibody and antibody fragment (such as scFv, Fab, Fc, F(ab')$_2$), and other genetically engineered portions of antibodies. Depending on the amino acid sequence of the constant domain of their heavy chains, immunoglobulins can be assigned to different classes. There are five major classes of immunoglobulins: IgA, IgD, IgE, IgG and IgM. Several of these may be further divided into subclasses (isotypes), e.g., IgG1, IgG2, IgG3, and IgG4; IgA1 and IgA2. The heavy chain constant domains that correspond to the different classes of immunoglobulins are called alpha ($\alpha$), delta ($\delta$), epsilon ($\epsilon$), gamma ($\gamma$), and mu ($\mu$), respectively. The subunit structures and three-dimensional configurations of different classes of immunoglobulins are well known. Preferably, the immunoglobulin recognizes and binds to alpha-4 integrin.

The term "antibody" is used in the broadest sense and specifically covers monoclonal antibodies (including agonist and antagonist antibodies), antibody compositions with polyepitopic specificity, and antibody fragments (e.g., Fab, F(ab')$_2$, scFv and Fv), so long as they exhibit the desired biological activity. "Antibody" is meant to include polyclonal antibodies, monoclonal antibodies, humanized antibodies, human antibodies, primatized7 antibodies and other antibodies produced via genetic engineering.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In addition to their specificity, the monoclonal antibodies are advantageous in that they are synthesized by mammalian cell expression systems or transgenic technology, uncontaminated by other immunoglobulins. For example, the monoclonal antibodies to be used in accordance with the present invention may be expressed in goats, as described by Behboodi, et al. (2002) *Transgenic cloned goats and the production of therapeutic proteins*. In *Principles of Cloning*. Elsevier Science (USA); and Meade et al. (1999). *Expression of recombinant proteins in the milk of transgenic animals in Gene expression systems: using nature for the art of expression*. J. M. Fernandez and J. P. Hoeffler ed., Academic Press. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the methods described by Shepherd et al., *Monoclonal Antibodies: A Practical Approach* (Oxford University Press, 2000).

The term "monoclonal antibodies" also includes "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. For example, the ability to bind to alpha-4 integrin. The "monoclonal antibodies" may also be isolated from phage antibody libraries using the techniques described for example in Clackson et al., 1991 *Nature* 352: 624-628 and Marks et al., 1991 *J. Mol. Biol.*, 222: 581-597. "Humanized" forms of non-human (e.g., murine, rabbit, bovine, equine, porcine, and the like) antibodies are chimeric immunoglobulins, immunoglobulin chains or fragments thereof (such as Fv, Fab, Fab', F(ab')$_2$ or other antigen-binding subsequences of antibodies), which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

The expression "linear antibodies" are also included by the general term "antibody" and are a pair of tandem Fd segments (VH-CH1-VH-CH1), which form a pair of antigen binding regions. Linear antibodies can be bispecific or monospecific.

A "variant antibody" (also included by the generic term "antibody") is a molecule which differs in amino acid sequence from a "parent" antibody's amino acid sequence by virtue of addition, deletion and/or substitution of one or more amino acid residue(s) in the parent antibody sequence. In the preferred embodiment, the variant comprises one or more amino acid substitution(s) in one or more hypervariable region(s) of the parent antibody. For example, the variant may comprise at least one substitution, e.g., from about one to about ten, and preferably from about two to about five, in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of the N-terminal, C-terminal, or internal extensions, deletions, or insertions into the antibody sequence should be construed as affecting sequence identity or homology.

To analyze such properties, one should compare a Fab form of the variant to a Fab form of the parent antibody or a full length form of the variant to a full length form of the parent antibody, for example, since it has been found that the format of the antibody impacts its activity in the biological, activity assays disclosed herein. The variant antibody of particular interest is one which displays at least about 10 fold, preferably at least about 20 fold, and most preferably at least about 50 fold, enhancement in biological activity when compared to the parent antibody. The "parent" antibody is one which is encoded by an amino acid sequence used for the preparation of the variant. Preferably, the parent antibody has a human framework region and has human antibody constant region(s). For example, the parent antibody may be a humanized or a human antibody.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Antibody fragments" comprise a portion of an intact antibody, generally the antigen binding or variable region of the intact antibody. Examples of antibody fragments include Fab, Fab', $F(ab')_2$, and Fv fragments; diabodies; linear antibodies; single-chain antibody molecules; and multispecific antibodies formed from antibody fragments. "Single-chain Fv" or "sFv" antibody fragments comprise the VH and VL domains of antibody, wherein these domains are present in a single polypeptide chain. Generally, the Fv polypeptide further comprises a polypeptide linker between the VH and VH domains which enables the sFv to form the desired structure for antigen binding.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. The route of antibody administration is in accord with known methods and are well known, and may include, for example, injection or infusion by intravenous, intraperitoneal, intracerebral, intramuscular, intraocular, intraarterial, or intralesional routes, or by sustained release systems. The antibody can be administered continuously by infusion or by bolus injection. Therapeutic antibody compositions generally are placed into a container having a sterile access port, for example, an intravenous solution bag or vial having a stopper pierceable by a hypodermic injection needle. "Pharmaceutically acceptable" excipients (e.g., vehicles, additives) are those which can reasonably be administered to a subject mammal to provide an effective dose of the active ingredient employed. A "stable" formulation is one in which the protein therein essentially retains its physical stability and/or chemical stability and/or biological activity upon storage. By "stable" is also meant a formulation which exhibits little or no signs of instability, including aggregation and/or deamidation. For example, the formulations provided by the present invention may remain stable for at least two year, when stored as indicated at a temperature of 5-8° C.

Various analytical techniques for measuring protein stability are available in the art and are reviewed in *Peptide and Protein Drug Delivery*, 247-301 (Vincent Lee ed., New York, N.Y., 1991) and Jones, 1993 *Adv. Drug Delivery Rev.* 10: 29-90, for examples. Stability can be measured at a selected temperature for a selected time period as exemplified by the provided examples. Storage of stable formulations if preferably for at least 6 months, more preferably 12 months, more preferably 12-18 months, and more preferably for 2 or more years.

A protein, such as an antibody or fragment thereof, "retains its physical stability" in a pharmaceutical formulation if it shows no signs of aggregation, precipitation, deamidation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity. Chemical stability can be assessed by detecting and quantifying chemically altered forms of the protein. Chemical alteration may involve size modification (e.g., clipping), which can be evaluated using size exclusion chromatography, SDS-PAGE and/or matrix-assisted laser desorption ionization/time-of-flight mass spectrometry (MALDI/TOF MS), for examples. Other types of chemical alteration include charge alteration (e.g., occurring as a result of deamidation), which can be evaluated by ion-exchange chromatography, for example. An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention has a pH in the range from about 3.0 to about 7.5; preferably from about pH 4.0 to about 7.0; more preferably from about pH 5.0 to about 6.5; and most preferably has a pH of about 6.0∀0.5. A pH of any point in between the above ranges is also contemplated.

In a pharmacological sense, in the context of the present invention, a "therapeutically effective amount" of an antibody refers to an amount effective in the prevention or treatment of a disorder for the treatment of which the antibody is effective. A "disorder" is any condition that would benefit from treatment with the antibody or protein. This includes chronic and acute disorders or diseases including those pathological conditions which predispose the mammal to the disorder in question.

"Treatment" refers to both therapeutic treatment and prophylactic or preventative measures. Those in need of treatment include those already with the disorder as well as those in which the disorder is to be prevented.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

By "patient" or "subject" is meant to include any mammal. A "mammal," for purposes of treatment, refers to any animal classified as a mammal, including but not limited to humans, domestic and farm animals, and zoo, sports, or pet animals, such as dogs, horses, cats, cows, and the like. Preferably, the mammal is human.

By "Antegren7" and is meant to include the antibody also known as AN100226 (antibody code number) or natalizumab (USAN name). Natalizumab is a recombinant, humanized anti-alpha-4 integrin antibody. Preferably the disease or condition being treated in the mammal is one which is modulated when a therapeutically effective dose of natalizumab is administered.

By "stable" is meant a formulation which exhibits little or no signs of instability, including aggregation and/or deamidation. In addition, "stable" may also refer to a formulation which does not exhibit any signs of instability for greater than or equal to two years, when stored as indicated at General Description In the discussion below and the examples to follow, formulations for stable antibody formulations are disclosed. Certain stable formulations disclosed have high concentrations of antibody but maintain a fixed volume, wherein the antibodies in these formulations are stable and the antibody does not precipitate out of solution or aggregate. Proteins other than antibodies are also contemplated for the high concentration formulations.

Antibodies are typically administered to a subject (e.g., a human) at a concentration of about 0.01 mg/mL to about 200 mg/mL. More typically, antibodies range in concentration from about 0.1 mg/mL to about 150 mg/mL. However, instances exist when greater concentrations are required to be administered to a patient, e.g., about 15 to about 200 mg/mL, more preferably about 15 mg/mL to 150 mg/mL, more preferably about 20 to about 50 mg/mL, and most preferably about 20 mg/mL and any integer value in between.

The antibody formulation may be administered to a mammal in need of treatment with the protein, in accordance with known methods. These methods may include, but are not limited to intravenous administration as a bolus or by continuous infusion over a period of time, by intramuscular, intraperitoneal, intracerebrospinal, subcutaneous, intra-articular, intrasynovial, intrathecal, oral, topical, or inhalation routes. In preferred embodiments, the antibody formulation is administered to the mammal by intravenous administration.

The appropriate dosage of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question. As used herein, two (or more) agents are said to be administered in combination when the two agents are administered simultaneously or are administered independently in a fashion such that the agents will act contemporaneously.

In practicing the methods of this invention, the compounds of this invention may be used alone or in combination, or in combination with other therapeutic agents. In certain preferred embodiments, the compounds of this invention may be co-administered along with other compounds typically prescribed for these conditions according to generally accepted medical practice. For example, the formulations of this invention can be administered in combination with other therapeutic agents or physical therapies for the treatment of rheumatoid arthritis, multiple schlerosis and Crohn's Disease.

2.1 Method of Making the Antibody Formulation

The process can be altered as would be known to the skilled artisan, but generally would follow a procedure such as the following. Obtain an ampoule from a working cell bank which contains cells which make the antibody or protein of interest. Prepare the inoculum. Culture or ferment the cells with additional feedings as is necessary. Harvest/clarify the cells by centrifugation and/or filtration. This can be done for example by concentrating the cells 10 fold by spiral wound filtration. Filter by a 0.2 Φm intermediate filtration followed by purification by protein A Sepharose Fast Flow7 (i.e., affinity chromatography) and reverse elution. The antibody containing composition then receives a treatment at pH 3.6-3.7. The mixture then receives a viral filtration followed by a concentration/diafiltration step. The composition can then be purified by DEAE Sepharose Fast Flow7 (anion exchange). This step can be performed multiple times. From this point, the composition is then further concentrated followed by a purification step using Sephacryl S300HR7 (i.e., gel filtration chromatography) system, wherein the running buffer used is phosphate/NaCl. The antibody containing composition can be further concentrated for the high concentration formulations (e.g., 20 mg/mL or more) if so desired. The antibody containing composition is then further buffered and the concentration adjusted by adding 0.02% (w/v) polysorbate 80. This composition then receives a final filtration using a 0.2 Φm filter and can be dispensed at this point into 100 mL to 10 L polypropylene bottles. The antibody or immunoglobulin so obtained can then be QC tested and QA released.

The above can be done, for example for natalizumab, as diagramed below:

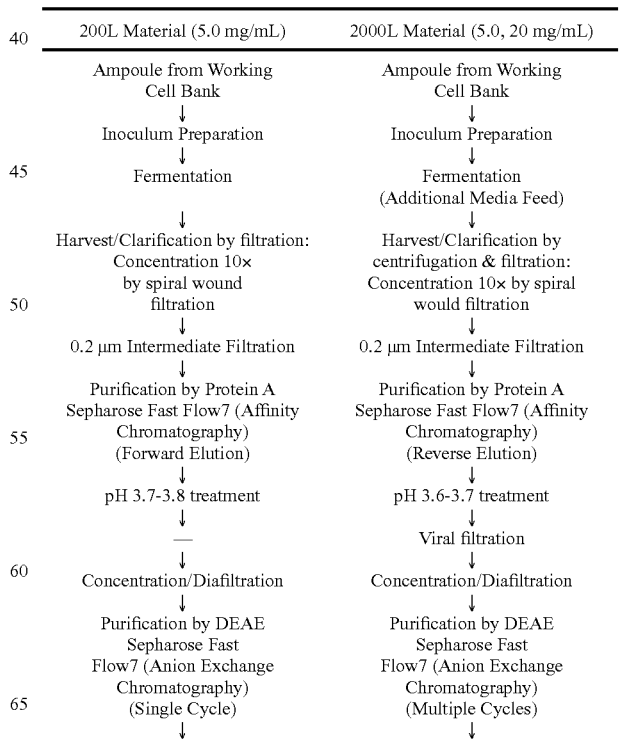

| 200L Material (5.0 mg/mL) | 2000L Material (5.0, 20 mg/mL) |
|---|---|
| Ampoule from Working Cell Bank | Ampoule from Working Cell Bank |
| ↓ | ↓ |
| Inoculum Preparation | Inoculum Preparation |
| ↓ | ↓ |
| Fermentation | Fermentation (Additional Media Feed) |
| ↓ | ↓ |
| Harvest/Clarification by filtration: Concentration 10× by spiral wound filtration | Harvest/Clarification by centrifugation & filtration: Concentration 10× by spiral would filtration |
| ↓ | ↓ |
| 0.2 µm Intermediate Filtration | 0.2 µm Intermediate Filtration |
| ↓ | ↓ |
| Purification by Protein A Sepharose Fast Flow7 (Affinity Chromatography) (Forward Elution) | Purification by Protein A Sepharose Fast Flow7 (Affinity Chromatography) (Reverse Elution) |
| ↓ | ↓ |
| pH 3.7-3.8 treatment | pH 3.6-3.7 treatment |
| ↓ | ↓ |
| — | Viral filtration |
| ↓ | ↓ |
| Concentration/Diafiltration | Concentration/Diafiltration |
| ↓ | ↓ |
| Purification by DEAE Sepharose Fast Flow7 (Anion Exchange Chromatography) (Single Cycle) | Purification by DEAE Sepharose Fast Flow7 (Anion Exchange Chromatography) (Multiple Cycles) |
| ↓ | ↓ |

-continued

| 200L Material (5.0 mg/mL) | 2000L Material (5.0, 20 mg/mL) |
|---|---|
| Concentration<br>↓<br>Purification by Sephacryl<br>S300HR7<br>(Gel Filtration Chromatography)<br>(Running Buffer:<br>histidine/NaCl)<br>↓<br>—<br><br>↓<br>Buffer & Concentration<br>Adjustment<br>Phosphate/NaCl, 0.02% (w/v)<br>polysorbate 80<br>↓<br>0.2 μm Final Filtration and<br>Dispensing<br>(100 mL-1 L polypropylene bottles)<br>↓<br>QC Testing and QA Release of<br>Bulk Purified AN100226 | Concentration<br>↓<br>Purification by Sephacryl<br>S300HR7<br>(Gel Filtration Chromatography)<br>(Running Buffer:<br>phosphate/NaCl)<br>↓<br>(Additional concentration for<br>20 mg/mL)<br>↓<br>Buffer & Concentration<br>Adjustment<br>(add 0.02% (w/v)<br>polysorbate 80)<br>↓<br>0.2 μm Final Filtration and<br>Dispensing (100<br>mL-10 L polypropylene bottles)<br>↓<br>QC Testing and QA Release of<br>Bulk Purified AN100226 |

2.2 The Antibody Formulation

In one aspect of the invention, an immunoglobulin is formulated in concentrations of about 1.7, 5.0, 10.0, 15.0, 20.0, 25.0, 30.0, 40.0 or 50.0 mg/mL in 10 mM sodium phosphate, 140 mM NaCl (pH 6.0∀0.5) and 0.02% polysorbate 80. If necessary, the pH is adjusted to 6.0∀0.5 with phosphoric acid.

One example of the different formulations is displayed below.

Quantitative Composition: Phosphate Buffer Formulation

| Component | Function | Unit Formula (per mL) 1.7 mg/mL | Unit Formula (per mL) 5.0 mg/mL | Unit Formula (per mL) 20 mg/mL |
|---|---|---|---|---|
| Active Ingredient: | | | | |
| Anti-α4 integrin humanized monoclonal antibody | Active | 1.7 mg | 5.0 mg | 20 mg |
| Other Ingredients: | | | | |
| Sodium Phosphate, USP | Buffer and tonicity | 1.4 mg | 1.4 mg | 1.4 mg |
| Sodium chloride, USP | Buffer and tonicity | 8.2 mg | 8.2 mg | 8.2 mg |
| phosphoric acid, NF | Adjust pH to 6.0 ∀ 0.5 | QS | QS | QS |
| Polysorbate 80, NF | Inhibit protein aggregation | 0.2 mg | 0.2 mg | 0.2 mg |
| Water for Injection, USP | Diluent | QS to 1 mL | QS to 1 mL | QS to 1 mL |

Any of the above formulations are optimally vialed in an aseptic vial. These vials can be, for example, Type I EP neutral glass vials (e.g., 5.0 or 20 mL fill vials) with Helvoet Pharma V9145/FM 157/1 gray butyl rubber stoppers with aluminum seals. However other suitable aseptic vials are also contemplated. For example, the formulations can be bottled as follows:

BOTTLING

Compounding of phosphate/sodium chloride/polysorbate 80 buffer, if needed
↓
Sterilization of vials, stoppers and manufacturing equipment
↓
Dilution with phosphate/sodium chloride/polysorbate 80 buffer antibody to 1.7 or 50 mg/mL, as required
↓
Sterile filtration
↓
Aseptic filling and stoppering of vials
Capping
↓
Release Testing More specifically, natalizumab obtained for example by the procedures discussed above, can be bottled as follows. Natalizumab 200 L and 2000 L drug product can be filled on a fully automated filling line equipped with a vial washing, sterilization and depyrogenation tunnel. Stoppers, seals and filling equipment are washed and sterilized prior to use. This process allows for large scale filling operations consistent with the volumes produced from the 2000 L fermentation.

When necessary, the formulation buffer, about 10 mM phosphate, about 140 mM NaCl, pH 6.0∀0.5, about 0.02% polysorbate 80, can be compounded in a Class 10,000 suite and used to dilute the bulk drug product to the final concentration. In-process specifications of concentration, pH and density are preferably reached prior to filtration.

The formulated natalizumab or other immunoglobulin can be sterile filtered through a 0.2 μm Millipak filter into a stainless steel surge tank inside the sterile core. Filling, stoppering and capping of natalizumab is fully automated. In-process samples for bulk sterility are collected; fill weight and headspace testing is conducted throughout the filling operation. Filled drug product is stored under refrigeration at about 2-8EC.

Filling occurs within a fully validated Class 100 sterile core. The filling line is validated to provide fill volumes within expected tolerances for the 5.0 mL and 20 mL fill volumes. Comprehensive environmental monitoring is conducted throughout the filling operation and reviewed to verify continual compliance with this standard. Media fills are conducted on a quarterly basis to support aseptic filling operations.

Alternatively, the 200 L drug substance material produced can be bottled pursuant to the following example. Vials, filling needles, the filtration assembly and tubing are prepared and sterilized prior to use. Stoppers can be prepared by the supplier. The stoppers are then sterilized prior to filling.

Natalizumab drug product or other protein is filled on a semi-automatic filling line, with batch preparation of components, automated filling, immediate stoppering, and a subsequent capping operation. This operation is appropriate for small batch scale operations.

The final bulk solution is then sterile filtered through a 0.2 μm Millipak filter into a sterile glass receiving vessel within a Class 100 environment. Regular calibration and in-process checks ensure that the filling tolerance remains within ∀2%. Vials are stoppered and capped immediately. Filled drug product is preferably stored refrigerated at 2-8EC.

The glass receiving vessel can be any number of vials, but can for example be a 5.0 or 20 mL neutral glass vial Type I (EP) supplied by, for example, Epsom Glass or AMILCO or a 5.0 mL or 20 mL USP Type I borosilicate glass vial, supplied by, for example Kimble or Wheaton. These vials can use any means of closure suitable. Vial closures include, but are not limited to a 13 mm Helvoet Pharma V9145/FM 157/1 grey butyl rubber stopper or a 13 mm and 20 mm Helvoet Pharma V9145/FM 157/1 grey butyl rubber stopper or a 13 mm or 20 mm West 4432/50 gray butyl rubber stopper. The rubber-stoppered bottled is then sealed most typically using an aluminum seal, such as that manufactured by West.

Although the present invention has been described in detail with reference to examples below, it is understood that various modifications can be made without departing from the spirit of the invention, and would be readily known to the skilled artisan.

EXAMPLES

Example 1

Selection of Polysorbate 80

The typical method of administering natalizumab is intravenous. Intravenous administration requires the final formulation to be isotonic. A formulation of AN100226 (natalizumab), 5 mg/mL in 50 mM L-histidine, 150 mM NaCl, pH 6.0 was initially chosen (Formulation #1). During a Phase II study, protein precipitation of the antibody was observed during the dilution and introduction of natalizumab into the clinical dosing apparatus. Polysorbate 80 was introduced into the formulation (Formulation #2) to resolve the observed protein precipitation. Preferably, the polysorbate for use with the present invention is low in peroxide, i.e., polysorbate from Sigma, Product number P6479, Lot Number 071K7283.

The two factors that have been shown to accelerate the precipitation of the AN100226 antibody are the presence of trace levels of silicone oil and denaturation at the air-liquid interface. The silicone oil was introduced into the product upon use of standard lubricated polypropylene syringes equipped with siliconized rubber stoppers. The introduction of the silicone oil is sufficient to cause discernible antibody precipitation in Formulation #1 upon gentle agitation and room temperature storage. The aggregation, deamidation and subsequent precipitation caused by denaturation at the air-liquid interface has become more discernable problematic with the drug being shipped to more clinical sites. Both causes of protein precipitation have been resolved by the addition of polysorbate 80 at a concentration of 0.02% (w/v).

Formulation #2 shows comparable stability to the histidine/NaCl formulation (Formulation #1) in all protein characterization assays, while providing increased stability during product shipping and handling in the clinical setting.

The addition of polysorbate 80 to the formulation also overcomes the problem of precipitating or aggregating antibody when preparing formulations with higher protein content. Initial work focused on agitation-induced aggregation at high protein concentrations, including 50 mg/mL. By subjecting the material to agitation using a vortex-type mixer, aggregated species were detected by size exclusion-high performance liquid chromatography (SEC-HPLC). This model identified polysorbate 80 as an effective inhibitor of aggregation, while sucrose and other buffering components had little beneficial effect.

The effectiveness of the addition of 0.02% (w/v) polysorbate 80 in preventing agitation-induced precipitation at a protein concentration of 5 mg/mL was assessed following addition of 10 μL of a 10% polysorbate 80 solution to vials of natalizumab (Lot No. AN100226-0003). The vials were shaken on their sides along with several vials of natalizumab in Formulation #1 at 150 rotations per minute in a horizontal plane. Within 3 hours of this treatment at room temperature, the vials of Formulation #1 were laden with particles and appeared turbid while the vials with 0.02% (w/v) polysorbate 80 remained clear and free of particles.

The observed aggregation is presumed to be caused by the air-surface interface, as vials completely filled with AN100226 in the absence of polysorbate 80 were shaken for extended periods of time without additional particle formation being induced.

An evaluation of the ability of 0.02% (w/v) polysorbate 80 to inhibit the protein precipitation facilitated by trace levels of silicone was conducted. A vial of natalizumab (Lot No. AN100226-0003) was adjusted to 0.02% (w/v) polysorbate 80 and drawn into a commercially available, lubricated 60 mL polypropylene syringe. The material was allowed to stand for several hours at room temperature. Visual inspection confirmed that no precipitation was occurring. The material was then filtered through a 0.2 μm filter into a 5-mL vial and inspected and found to be substantially free of particles after several days, while vials treated in the same manner in the absence of polysorbate 80 (Formulation #1) were laden with particles.

Example 2

Selection of the Phosphate Buffer

During release testing of the histidine placebo (containing 0.02% w/v polysorbate 80), new trace impurities were detected. These impurities arose from degradation of polysorbate 80, apparently through an oxidation reaction involving metal ions and histidine. For active natalizumab drug product, these trace impurities have been detected only after storage at elevated temperatures (e.g., 25EC and 40EC). Thus, the decision was made to modify the placebo and use phosphate to replace histidine in the buffer. The lot of histidine used in the product placebo was different than that used for the active natalizumab drug product lots AN100226-004 and AN100226-005. The impact of the source of histidine on polysorbate 80 degradation is discussed in greater detail infra.

During testing of the placebo, trace impurities were detected in the histidine/NaCl/0.02% (w/v) polysorbate 80 placebo (Formulation #2). These impurities were detected by their absorbency in the low wavelength ultraviolet region. The absorbency profiles from 200 to 400 nm for placebo stored at 5EC, 25EC, and 40EC for one month were determined. These data indicate that the impurities are increasing as a function of temperature.

The size exclusion HPLC method used to monitor antibody aggregation was modified to increase sensitivity for detection of the trace impurities by increasing the column load 5-fold to 100 μL, and the sample is applied undiluted rather than 10-fold diluted. In addition, the absorbency is monitored at 260 nm to reflect the absorbency maximum of the impurities. The method provides a tool to evaluate the presence of these trace impurities in both placebo and product, as the antibody emerges much earlier in the elution profile.

Placebo and natalizumab final drug product formulated in Formulations #1 and #2 were analyzed by the SEC-HPLC method described above. Analysis of the placebo in Formulation #1 spiked with polysorbate 80 to 0.02% (w/v) was performed just prior to chromatography. This shows the UV absorbency of polysorbate 80, histidine, and salt in the absence of the trace impurities. The broad peak at 16 minutes is associated with polysorbate 80 while the peaks at approximately 26-27 minutes are attributed to histidine and salt. The histidine/NaCl/0.02% (w/v) polysorbate 80 placebo (Formulation #2) stored at 5EC for two months shows a marked increase in the late eluting peaks which implicates polysorbate 80 in the production of these impurities. In addition, the eluting at 16 minutes disappeared, indicating that the polysorbate 80 has been degraded.

AN100226 stored as bulk drug substance for approximately 5 months at 5EC in Formulation #1 was analyzed after spiking with polysorbate 80 to 0.02% (w/v) just prior to chromatography. The antibody elutes at 16-18 minutes using these overload conditions. The remainder of the profile resembles the placebo with polysorbate 80 spike. The two-month stability samples for natalizumab lot #AN100226-0004 were also analyzed by this method. The elution profile for the 5EC natalizumab sample indicates the absence of any additional peaks and comparable levels of the histidine/salt peaks at 26-27 minutes. The trace impurities are detected at two months for the 25EC sample, and elevated levels are present for the two month 40EC sample. Thus, these impurities have not been detected in the clinical supplies, which are stored at 5EC. The appearance of these trace impurities is occurring much more rapidly in placebo than in natalizumab.

To avoid the formation of these impurities in the placebo, histidine was replaced with inorganic buffering components in the placebo formulation. The placebo product for the clinical trials is a sterile isotonic phosphate buffered solution with 0.02% (w/v) polysorbate 80 at pH 6.0. The substitution of histidine with phosphate was demonstrated to significantly reduce the rate of polysorbate 80 degradation. 100 µL of the phosphate/NaCl/0.02% (w/v) polysorbate 80 placebo formulation was analyzed by size exclusion HPLC monitored at 260 nm both at time zero and after 3 days at 60EC. Little change is seen in the SEC-HPLC profile as a result of this incubation. The SEC-HPLC profile for the histidine/NaCl/0.02% (w/v) polysorbate 80 formulation following only two days at 60EC shows significant levels of trace impurities related to the degradation of polysorbate 80. These data demonstrate that the polysorbate 80 degradation is significantly impeded by replacing histidine with phosphate in the placebo formulation.

Example 3

Natalizumab Formulation with Polysorbate 80 and Histidine Combined

The mechanism by which these trace impurities are produced is thought to be through a metal catalyzed oxidation of polysorbate (see Donbrow et al., 1978 *J. Pharmaceutical Sciences*, 67(12): 28). Donbrow describes that autoxidation during storage occurs for different types of polysorbate (e.g., polysorbate 20). Light, temperatures and metal ions also impact autoxidation. Donbrow et al. (1978). It has been confirmed that both histidine and polysorbate 80 are required for this reaction to proceed at a significant rate. Ajinomoto is the single histidine source used for formulation. However significant differences in the rate of reaction between lots supplied by the Ajinomoto have been observed.

An additional factor that plays a role in accelerating the reaction is the presence of metal. This was demonstrated by running a reaction at 60EC for five days in glass vessel with 50 mM histidine (Lot No. R016A008) and 2% (w/v) polysorbate 80. Under these conditions, minimal levels of the trace impurities are produced for this histidine lot. The reaction was then split into three vessels: (1) the first vessel remained as the control; (2) a gray butyl container closure (stopper) was added to the second vessel; and (3) a stainless steel needle was added to the third vessel. These reactions were then run for four days at 60EC and analyzed by a UV scan from 200 to 400 nm. The reaction progressed further over this time period in the presence of the needle.

Example 4

Evaluation of Impurities X Mouse Single-Dose Limit Test

The potential toxicity of these impurities was evaluated in a mouse single-dose limit test. Histidine placebo and natalizumab samples in Formulation #2 stored at 40EC for six weeks were used because these samples provide the largest amount of the impurities. There were no signs of toxicity due to the impurities. Preliminary data are provided in the non-clinical section of the submission.

The SEC-HPLC profiles for 100 µL injections of samples used in the mouse single-dose limit test were determined. The natalizumab sample in Formulation #1 spiked with polysorbate 80 prior to analysis has little 260 nm absorbing material eluting after 20 minutes. The peak eluting at 34 minutes was found in this lot of natalizumab without polysorbate 80 addition and therefore does not indicate polysorbate 80 degradation. By contrast, the placebo in Formulation #2 stored at 40EC for six weeks, showed complete degradation, as the total area under the curve was 12.8 million µVXseconds. The natalizumab sample in Formulation #2 and stored at 40EC for six weeks had less complete degradation. The analysis confirms that the samples stored at 40EC and tested in the mouse single-dose limit test are laden with degraded polysorbate 80.

Example 5

Establishing Impurity Specifications

To assess if partially degraded polysorbate 80 is still capable of preventing antibody aggregation, Formulation #2 was heated to 60EC for 3 days in the presence of a needle to convert all the polysorbate 80 to the maximum levels of impurities. The reaction was confirmed to have degraded all the polysorbate 80 by both SEC and reverse phase HPLC. This material was diluted one-to-one with a 10 mg/mL solution of AN100226 in Formulation #2 resulting in a solution containing 0.01% (w/v) polysorbate 80 and 50% of the maximum level of degraded polysorbate 80. These antibody solutions were exposed to both shaking and siliconized syringes for several hours; aggregation of the antibody was prevented. The control samples exposed to the same conditions but without polysorbate 80 showed significant precipitation.

It is concluded from this work that as long as no more than fifty percent of the polysorbate 80 is degraded, this material can provide the appropriate environment to prevent antibody aggregation.

Although very little polysorbate degradation is occurring in the active drug product, monitoring the isoelectric focusing (IEF) pattern is done to confirm that this formulation is not compromising the antibody. IEF profiles for the six week stability time points for 5EC, 25EC and 40EC storage conditions were determined. Both the 5EC and 25EC samples are comparable to the reference standard, with no evidence of any change in overall charge of the protein. The 40EC sample showed the shift to a more acidic species typical of this product in a liquid formulation either in the presence or absence of polysorbate 80.

To establish a relationship between the extent of polysorbate 80 degradation and the peak area from the SEC-HPLC, a dilution series for six concentrations of degraded polysorbate 80 from 0 to 50% was evaluated. Formulation #2 was heated to 60EC for 3 days with a needle and confirmed to be 100% degraded by SEC and reverse phase HPLC. The reaction mixture was then diluted with AN100226 purified bulk in Formulation #1, freshly spiked with 0.02% (w/v) polysorbate 80 and analyzed by SEC-HPLC. The SEC profiles were monitored at 260 nm.

The data from this dilution series were plotted by the total peak area integrated (μVXseconds) for the absorbency profile after approximately 24 minutes as a function of the ratio of degraded polysorbate 80. This plot indicates that an area of less than 5 million μVXseconds represents about a 50% loss of polysorbate 80 to degradation products. There is a direct relationship between the amount of oxidized polysorbate 80 added and the peak area for the peaks eluting late in the chromatogram.

A preliminary limit for these trace impurities in natalizumab has been established based on the mouse single-dose limit test, the antibody solubility data with 50% degraded polysorbate 80, and estimates of the extent of the polysorbate 80 degradation. The method has been included in the ongoing stability program and a limit has been established. If additional lots are manufactured with histidine buffer, these limits will be applied at time of release as well.

Limit: total area under the peaks after approximately 24 minutes is not to exceed $4 \times 10^6$ μVXseconds.

Example 6

1.7 mg/mL Natalizumab Formulation 1.7 mg Natalizumab
1.4 mg Sodium phosphate, USP
8.2 mg Sodium chloride, USP
0.2 mg Polysorbate 80, NF
Adjust pH to 6.0∀0.5 with phosphoric acid, NF. QS to 1 mL. With preferred storage at 5-8EC.

Example 7

5.0 mg/mL Natalizumab Formulation 5.0 mg Natalizumab
1.4 mg Sodium phosphate, USP
8.2 mg Sodium chloride, USP
0.2 mg Polysorbate 80, NF
Adjust pH to 6.0∀0.5 with phosphoric acid, NF. QS to 1 mL. With preferred storage at 5-8EC.

Example 8

20 mg/mL Natalizumab Formulation 20.0 mg Natalizumab
1.4 mg Sodium phosphate, USP
8.2 mg Sodium chloride, USP
0.2 mg Polysorbate 80, NF
Adjust pH to 6.0∀0.5 with phosphoric acid, NF. QS to 1 mL. With preferred storage at 5-8EC.

Example 9

50.0 mg/mL Natalizumab Formulation 50.0 mg Natalizumab
1.4 mg Sodium phosphate, USP
8.2 mg Sodium chloride, USP
0.2 mg Polysorbate 80, NF
Adjust pH to 6.0∀0.5 with phosphoric acid, NF. QS to 1 mL. With preferred storage at 5-8EC.

Example 10

5.0 mg/mL Natalizumab Formulation 5.0 mg/mL natalizumab
140 mM NaCl
0.02% Polysorbate 80 (w/v)
10 mM sodium phosphate
Adjust pH to 6.0∀0.5 with phosphoric acid. Optimally store formulation at about 5EC to about 8EC.

Example 11

10 mg/mL Natalizumab Formulation 10.0 mg Natalizumab
1.4 mg Sodium phosphate, USP
8.2 mg Sodium chloride, USP
0.2 mg Polysorbate 80, NF
Adjust pH to 6.0∀0.5 with phosphoric acid, NF. QS to 1 mL. With preferred storage at 5-8EC.

Example 12

10 mg/mL Natalizumab Formulation 10.0 mg Natalizumab
1.4 mg Sodium phosphate, USP
8.2 mg Sodium chloride, USP
0.1 mg Polysorbate 80, NF
Adjust pH to 6.0∀0.5 with phosphoric acid, NF. QS to 1 mL. With preferred storage at 5-8EC.

Example 13

20 mg/mL Natalizumab Formulation 20.0 mg/mL Natalizumab
140 mM NaCl
0.02% Polysorbate 80 (w/v)
10 mM sodium phosphate
Adjust pH to 6.0∀0.5 with phosphoric acid and bring volume to 125 mL. Optimally store formulation at about 5EC to about 8EC.

Example 15

Lypholized Natalizumab Formulation

Additional liquid formulations of antibody at high concentration, from 20-200 mg/mL may consist of phosphate or other suitable buffer (such as histidine, citrate, acetate or succinate) in the concentration range of 2 to 50 mM, to provide buffering in the pH range of 3.0 to 7.0. Most preferably, the pH is 6.0, +/−0.5. The addition of polyols (such as sorbitol and mannitol), disaccharides (such as sucrose or trehalose) and amino acids (such as glycine) may be added in varying amounts with sodium chloride to maintain stability and provide an isotonic solution. The use of surfactants, such but not limited to the polysorbates, add stability when used in the range of 0.001 to 2%. To prepare a liquid formulation, natalizumab was concentrated to 65 mg/mL in 10 mM sodium phosphate, 140 mM sodium chloride, pH 6, with about 0.06% polysorbate 80. The resulting solution was slightly opalescent but without particulates. The sample contained greater than 99% monomer with no high molecular weight aggregate or low molecular weight species by SEC.

A stable lyophilized pharmaceutical formulation is provided. Because phosphate buffer undergoes a pH change during freezing, it is necessary to replace the phosphate with a different buffer. This buffer may be comprised of histidine, citrate or succinate, with the ability to buffer effectively in the pH range of 3.0 to 7.0, most preferably in the range of 6.0+/−0.5.

The use of polyols (such as mannitol) and sugars (such as sucrose) are necessary to provide cryo- and lyo-protection. These polyols may be used alone or in a combination to provide for stability and adjustment of the tonicity. Additionally, the use of amino acids (such as glycine), at levels of 10-1000 mM may used to prevent aggregation.

Surfactants, such as polysorbates or poloxamers, may be used at levels from 0.001% to 2.0% to provide for stability before lyophilization and after reconstitution and to provide for more rapid reconstitution times.

The protein, following the final purification step, may be formulated using ultrafiltration for concentration and diafiltration for buffer exchange. The protein may also be formulated using column chromatography for buffer exchange. Some combination of these techniques may also be used.

In addition, the final desired protein concentration may be obtained by filling at a protein and excipient concentration lower than desired and reconstitution at a smaller volume. For example, a 2.5 mL fill volume of a 40 mg/mL solution may be used, followed by reconstitution with 1 mL to obtain a 100 mg/mL solution.

For example, natalizumab, at a concentration of 20 mg/mL, was lyophilized in a solution containing 5 mM histidine, 20 mg/mL sucrose and 0.02% polysorbate 80, pH 6. The solution was filled at 5 mL per vial into 10 mL borosilicate glass vials and fitted with gray butyl rubber lyophilization stoppers. Lyophilization was done using a Virtis Gensis model lyophilizer. The product was frozen at a shelf temperature of −60° C. for 10 hours and then the shelf temperature was raised to −40°. Primary drying was performed at a shelf temperature of −10° C. and a chamber pressure of 100 mTorr for 20 hours. Secondary drying was achieved at a shelf temperature of 25° C. with a chamber pressure of 100 mTorr for 10 hours. The vials were stoppered under vacuum.

The vials were then reconstituted using 1 mL of sterile WFI to give a formulation containing 100 mg/mL natalizumab. The samples were analyzed immediately after lyophilization and after 2 wks of storage in the lyophilized form at 40 deg. In both cases reconstitution times were immediate. The reconstituted solutions were clear and colorless with an absence of particulate material. The samples contained greater than 99% monomer by SEC, with no high molecular weight aggregate, or low molecular weight species. After 2 weeks storage at 40 deg, the sample showed 94% potency relative to reference (specification 80-125%).

All cited patents and publications referred to in this application are herein incorporated by reference in their entirety for all purposes.

What is claimed is:

1. A method of treatment, comprising administering to a patient with multiple sclerosis a therapeutic amount of a stable, aqueous pharmaceutical formulation comprising from about 20 mg/ml to about 150 mg/ml of natalizumab, about 10 mM phosphate buffer, about 140 mM sodium chloride, and polysorbate 80 present in an amount of about 0.001% to 2% (w/v), wherein the multiple sclerosis is treated by administration of the stable, aqueous pharmaceutical formulation.

2. The method of claim 1, wherein the pharmaceutical formulation is administered to the patient by intravenous administration.

3. The method of 2, wherein the pharmaceutical formulation is administered to the patient over a series of treatments.

4. The method of claim 1, wherein natalizumab is present in an amount of about 20 mg/mL.

5. The method of claim 1, wherein the polysorbate 80 is present an amount of about 0.02% (w/v).

6. The method of claim 1, wherein the formulation has a pH of about 3.0 to about 7.0.

7. The method of claim 6, wherein the pH is about 5.5 to about 6.5.

8. The method of claim 6, wherein the pH is about 6.0 ±0.5.

9. A method treatment, comprising administering to a patient with Crohn's disease a therapeutic amount of a stable, aqueous pharmaceutical formulation comprising from about 20 mg/ml to about 150 mg/ml of natalizumab, about 10 mM phosphate buffer, about 140 mM sodium chloride, and polysorbate 80 present in an amount of about 0.001% to 2% (w/v), wherein the Crohn's disease is treated by administration of the stable, aqueous pharmaceutical formulation.

10. The method of claim 9, wherein the pharmaceutical formulation is administered to the patient by intravenous administration.

11. The method of 10, wherein the pharmaceutical formulation is administered to the patient over a series of treatments.

12. The method of claim 9, wherein natalizumab is present in an amount of about 20 mg/mL.

13. The method of claim 9, wherein the polysorbate 80 is present an amount of about 0.02% (w/v).

14. The method of claim 9, wherein the formulation has a pH of about 3.0 to about 7.0.

15. The method of claim 14, wherein the pH is about 5.5 to about 6.5.

16. The method of claim 15, wherein the pH is about 6.0 ±0.5.

17. The method of claim 1, wherein natalizumab is present in an amount of about 150 mg/mL.

18. The method of claim 9, wherein the pharmaceutical formulation is administered to the patient by subcutaneous administration.

19. The method of claim 17, wherein natalizumab is present in an amount of about 150 mg/mL.

20. The method of claim 19, wherein the pharmaceutical formulation is administered to the patient by subcutaneous administration.

21. A method of treatment, comprising intravenously administering to a patient with multiple sclerosis a therapeutic amount of a stable, aqueous pharmaceutical formulation comprising 20 mg/ml natalizumab, about 10 mM phosphate buffer, 8.18 mg/mL of sodium chloride, and 0.2 mg/mL of polysorbate 80, wherein the formulation has a pH of 6.1, and wherein the multiple sclerosis is treated by administration of the stable, aqueous pharmaceutical formulation.

22. A method of treatment, comprising intravenously administering to a patient with Crohn's disease a therapeutic amount of a stable, aqueous pharmaceutical formulation comprising 20 mg/ml natalizumab, about 10 mM phosphate buffer, 8.18 mg/mL of sodium chloride, and 0.2 mg/mL of polysorbate 80, wherein the formulation has a pH of 6.1, and wherein the Crohn's disease is treated by administration of the stable, aqueous pharmaceutical formulation.

* * * * *

UNITED STATES PATENT AND TRADEMARK OFFICE
CERTIFICATE OF CORRECTION

PATENT NO. : 8,815,236 B2  
APPLICATION NO. : 13/676866  
DATED : August 26, 2014  
INVENTOR(S) : David J. Burke et al.

Page 1 of 1

It is certified that error appears in the above-identified patent and that said Letters Patent is hereby corrected as shown below:

IN THE CLAIMS:

Claim 8, column 18, line 17, "6" should read --7--.

Claim 18, column 18, line 45, "9" should read --17--.

Claim 19, column 18, line 48, "17" should read --9--.

Signed and Sealed this  
Third Day of February, 2015

Michelle K. Lee  
*Deputy Director of the United States Patent and Trademark Office*